US010966682B2

(12) United States Patent
Maruyama et al.

(10) Patent No.: US 10,966,682 B2
(45) Date of Patent: Apr. 6, 2021

(54) CAPACITIVE MICROMACHINED ULTRASONIC TRANSDUCER AND INFORMATION ACQUISITION APPARATUS INCLUDING CAPACITIVE MICROMACHINED ULTRASONIC TRANSDUCER

(71) Applicant: CANON KABUSHIKI KAISHA, Tokyo (JP)

(72) Inventors: Ayako Maruyama, Sagamihara (JP); Kazutoshi Torashima, Yokohama (JP); Atsushi Kandori, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 358 days.

(21) Appl. No.: 15/770,427

(22) PCT Filed: Oct. 12, 2016

(86) PCT No.: PCT/JP2016/004553
§ 371 (c)(1),
(2) Date: Apr. 23, 2018

(87) PCT Pub. No.: WO2017/068761
PCT Pub. Date: Apr. 27, 2017

(65) Prior Publication Data
US 2018/0310915 A1   Nov. 1, 2018

(30) Foreign Application Priority Data
Oct. 24, 2015   (JP) .............................. JP2015-209430

(51) Int. Cl.
*A61B 8/00*   (2006.01)
*A61B 8/14*   (2006.01)
(Continued)

(52) U.S. Cl.
CPC .......... *A61B 8/4483* (2013.01); *A61B 5/0095* (2013.01); *A61B 8/14* (2013.01);
(Continued)

(58) Field of Classification Search
CPC ........... A61B 8/00; A61B 5/0095; A61B 8/14; A61B 2562/028; A61B 8/4483–4494;
(Continued)

(56) References Cited

U.S. PATENT DOCUMENTS 4,197,750 A * 4/1980 Hassler .................. G01N 29/06
                                              367/46
5,410,605 A * 4/1995 Sawada ................ G10K 11/178
                                              381/71.14
(Continued)

FOREIGN PATENT DOCUMENTS

JP    2014-197846 A    10/2014
JP    2015-100093 A    5/2015

OTHER PUBLICATIONS

Caronti ["A Low-Noise, Wideband Electronic System for Pulse-Echo Ultrasound Imaging with CMUT Arrays", 2004 IEEE International Ultrasonics, Ferroelectrics, and Frequency Control Joint 50th Anniversary Conference] (Year: 2004).*
(Continued)

*Primary Examiner* — Oommen Jacob
(74) *Attorney, Agent, or Firm* — Canon U.S.A., Inc. IP Division

(57) ABSTRACT

A capacitive micromachined ultrasonic transducer having a wide reception band is provided.
The capacitive micromachined ultrasonic transducer includes an element including a first sub-element and a second sub-element each including a cell. The cell includes a vibrating membrane that includes one of two electrodes formed with a spacing therebetween and that is vibratably
(Continued)

supported. The capacitive micromachined ultrasonic transducer further includes a first detection circuit, a second detection circuit, and a combining circuit that combines a signal from the first detection circuit and a signal from the second detection circuit. The first sub-element is electrically connected to the first detection circuit, and the second sub-element is electrically connected to the second detection circuit. The first detection circuit and the second detection circuit have different cut-off frequencies.

15 Claims, 12 Drawing Sheets

(51) Int. Cl.
  A61B 5/00    (2006.01)
  B06B 1/02    (2006.01)
  G01S 7/52    (2006.01)
  G01S 15/89   (2006.01)
(52) U.S. Cl.
  CPC .......... *A61B 8/4494* (2013.01); *B06B 1/0246* (2013.01); *B06B 1/0269* (2013.01); *B06B 1/0292* (2013.01); *G01S 7/52025* (2013.01); *G01S 7/52079* (2013.01); *G01S 15/8929* (2013.01); *A61B 2562/028* (2013.01); *B06B 2201/51* (2013.01)
(58) Field of Classification Search
  CPC ............. G01S 7/52079; G01S 7/52025; G01S 15/8929; B06B 2201/51; B06B 1/00; B06B 3/00; G01N 29/2406
  See application file for complete search history.

(56) References Cited

U.S. PATENT DOCUMENTS

| | | | |
|---|---|---|---|
| 5,870,351 A | 2/1999 | Ladabaum et al. | |
| 6,829,131 B1* | 12/2004 | Loeb | H04R 19/005 361/115 |
| 7,274,623 B2 | 9/2007 | Bayram | B06B 1/0292 310/324 |
| 9,314,820 B2* | 4/2016 | Akiyama | G01N 29/2418 |
| 9,636,707 B2* | 5/2017 | Ikeda | B06B 1/0292 |
| 2002/0030690 A1* | 3/2002 | Someya | G09G 5/005 345/598 |
| 2002/0048220 A1* | 4/2002 | Khuri-Yakub | G01H 11/06 367/181 |
| 2005/0254805 A1* | 11/2005 | Moriya | H04N 5/23248 396/53 |
| 2006/0007045 A1* | 1/2006 | Fiasca | G01S 15/8927 343/700 MS |
| 2007/0059858 A1* | 3/2007 | Caronti | B06B 1/0292 438/50 |
| 2008/0259725 A1* | 10/2008 | Bayram | B06B 1/0292 367/7 |
| 2009/0048522 A1* | 2/2009 | Huang | B06B 1/0292 600/459 |
| 2010/0254222 A1* | 10/2010 | Huang | B06B 1/0292 367/181 |
| 2012/0038242 A1* | 2/2012 | Tanaka | G10K 9/121 310/300 |
| 2012/0194107 A1* | 8/2012 | Kandori | B06B 1/0246 318/116 |
| 2013/0064043 A1* | 3/2013 | Degertekin | G01S 15/8925 367/137 |
| 2013/0116568 A1* | 5/2013 | Certon | A61B 8/145 600/447 |
| 2013/0233159 A1* | 9/2013 | Kuroki | H04R 3/005 84/736 |
| 2013/0293065 A1* | 11/2013 | Hajati | B06B 1/0629 310/334 |
| 2014/0219062 A1* | 8/2014 | Rothberg | B81B 7/0077 367/135 |
| 2014/0236017 A1* | 8/2014 | Degertekin | B06B 1/02 600/462 |
| 2014/0251017 A1* | 9/2014 | Kandori | G01N 29/2418 73/661 |
| 2015/0032002 A1* | 1/2015 | Rothberg | A61B 8/4488 600/440 |
| 2015/0038856 A1* | 2/2015 | Houlton | A61B 5/6826 600/484 |
| 2015/0087991 A1* | 3/2015 | Chen | G01S 7/5208 600/459 |
| 2018/0310915 A1* | 11/2018 | Maruyama | A61B 5/0095 |

OTHER PUBLICATIONS

Bayram ["Finite Element Modeling and Experimental Characterization of Crosstalk in 1-D CMUT Arrays", ieee transactions on ultrasonics, ferroelectrics, and frequency control, vol. 54, No. 2, Feb. 2007] (Year: 2007).*

Guldiken ["Dual-Electrode CMUT With Non-Uniform Membranes for High Electromechanical Coupling Coefficient and High Bandwidth Operation", IEEE Transactions on Ultrasonics, Ferroelectrics, and Frequency Control, vol. 56, No. 6, Jun. 2009] (Year: 2009).*

Satir ["A Large-Signal Model for CMUT Arrays with Arbitrary Membrane Geometry Operating in Non-Collapsed Mode", IEEE Transactions on Ultrasonics, Ferroelectrics, and Fr 2426 equency Control, vol. 60, No. 11, Nov. 2013] (Year: 2013).*

Huang ["Capacitive Micromachined Ultrasonic Transducers with Piston-Shaped Membranes: Fabrication and Experimental Characterization", IEEE Transactions on Ultrasonics, Ferroelectrics, and Frequency Control, vol. 56, No. 1, Jan. 2009] (Year: 2009).*

Arezoo ["IMultiple Moving Membrane CMUT With Enlarged Membrane Displacement and Low Pull-Down Voltage", IEEE Electron Device Letters, Vol. 34, No. 12, Dec. 2013] (Year: 2013).*

* cited by examiner

[Fig. 1]
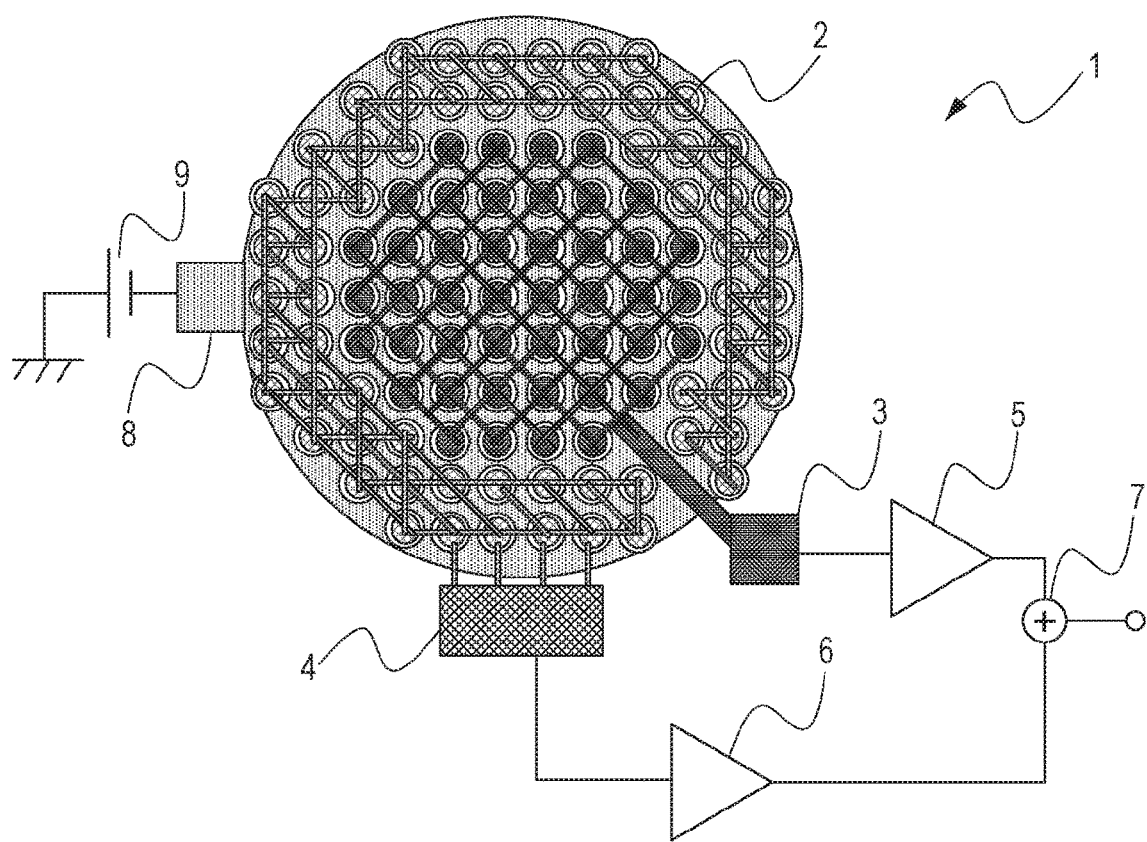

[Fig. 2]
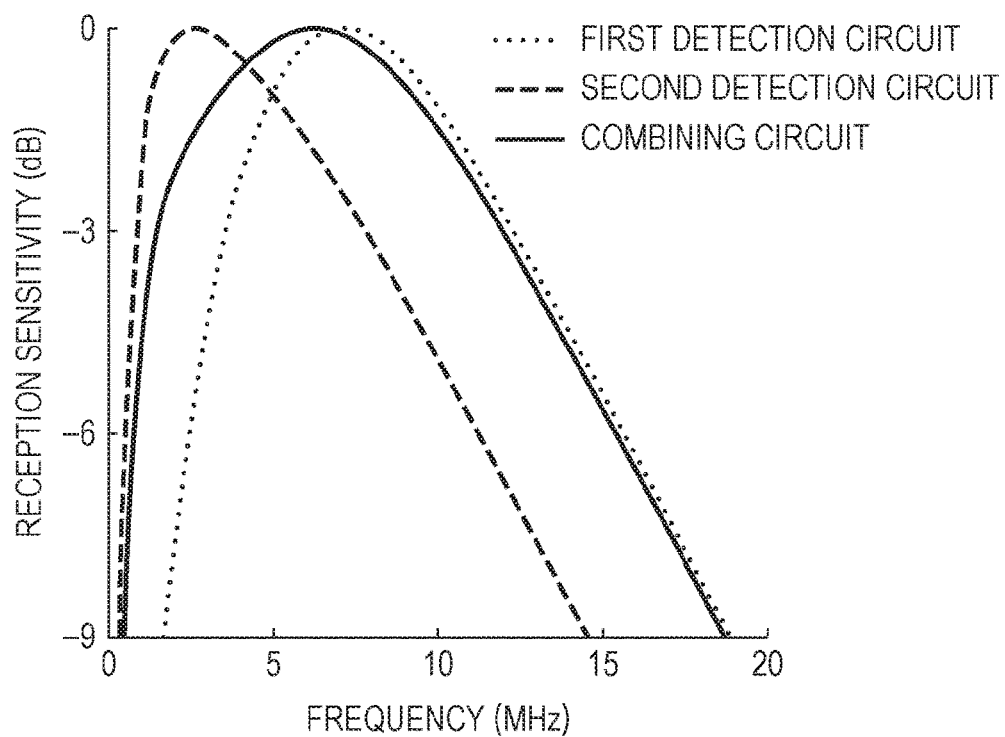
[Fig. 3]
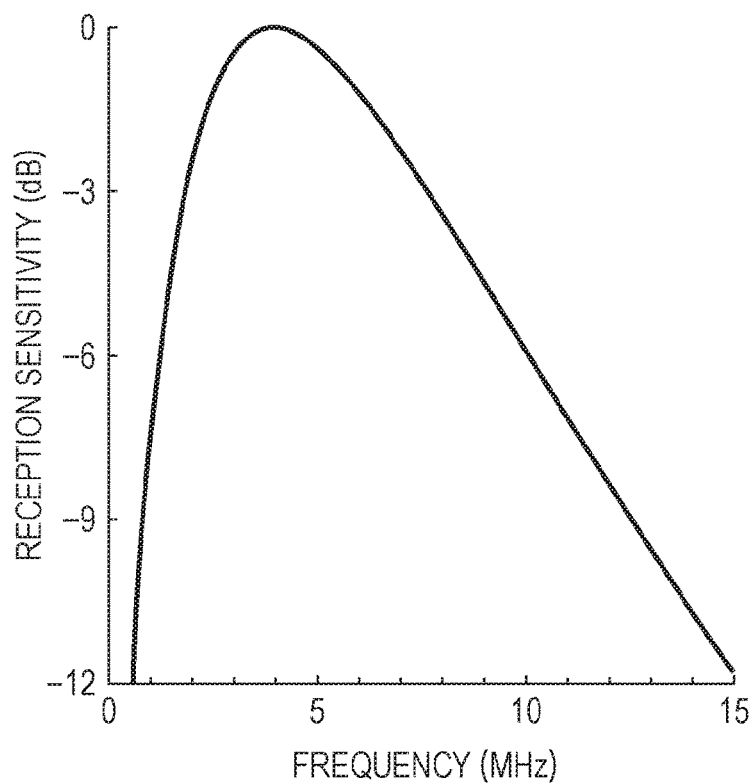

[Fig. 4]
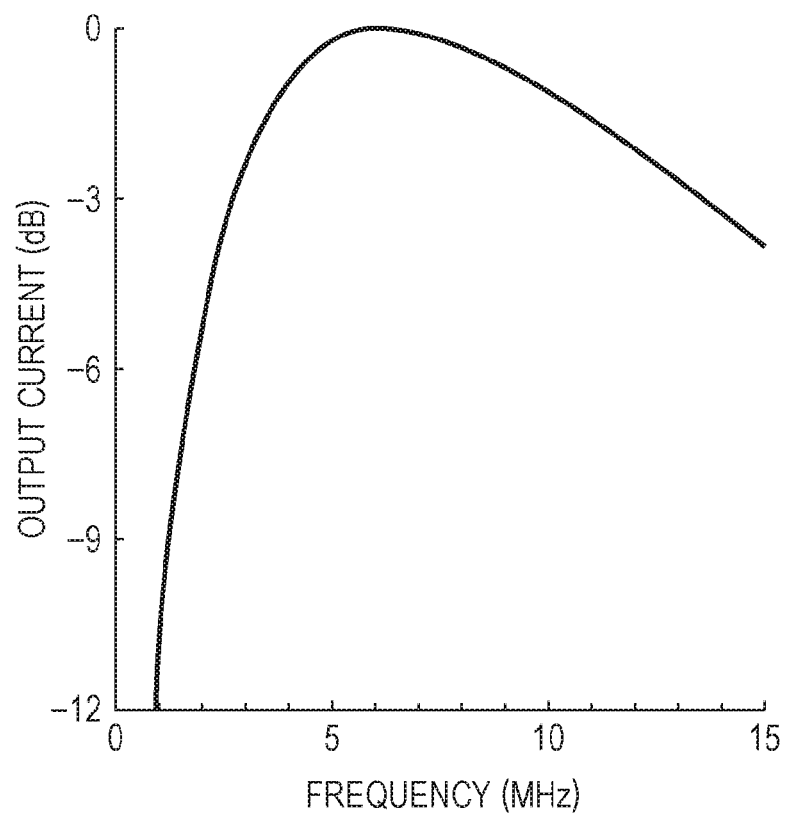
[Fig. 5]
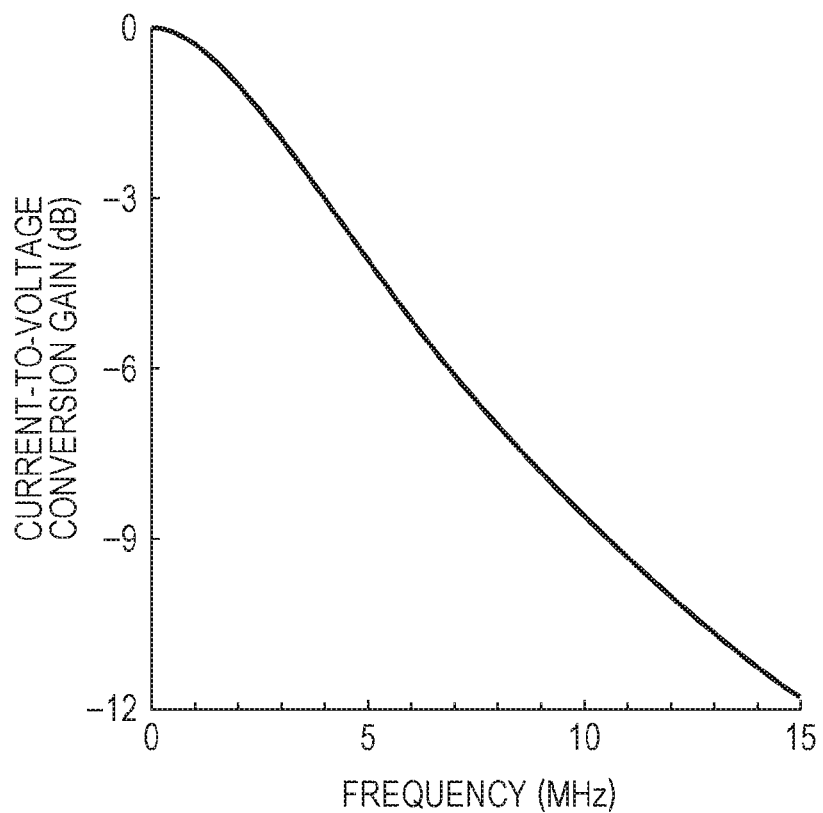

[Fig. 6]
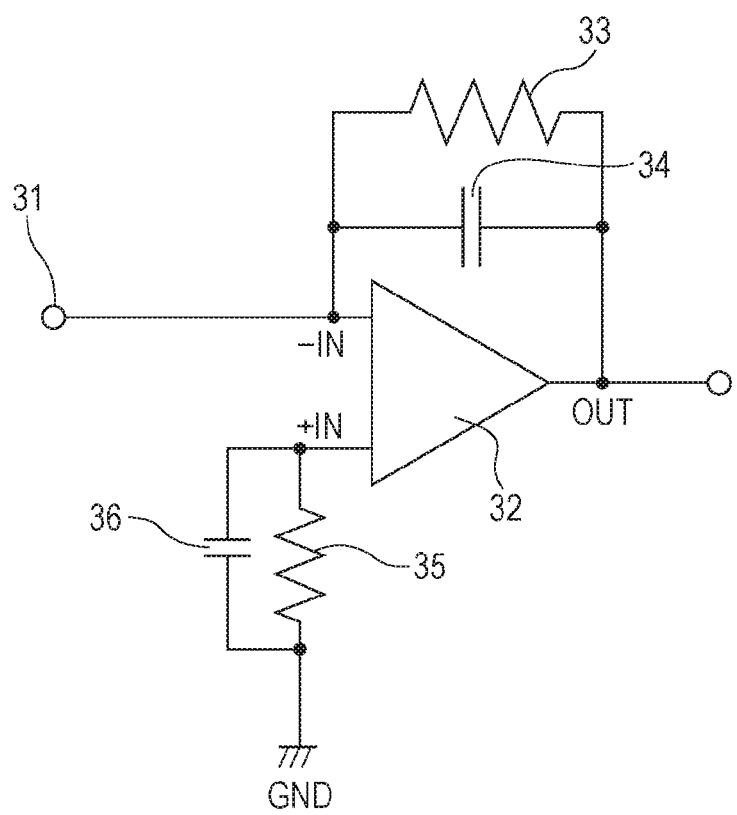

[Fig. 7]
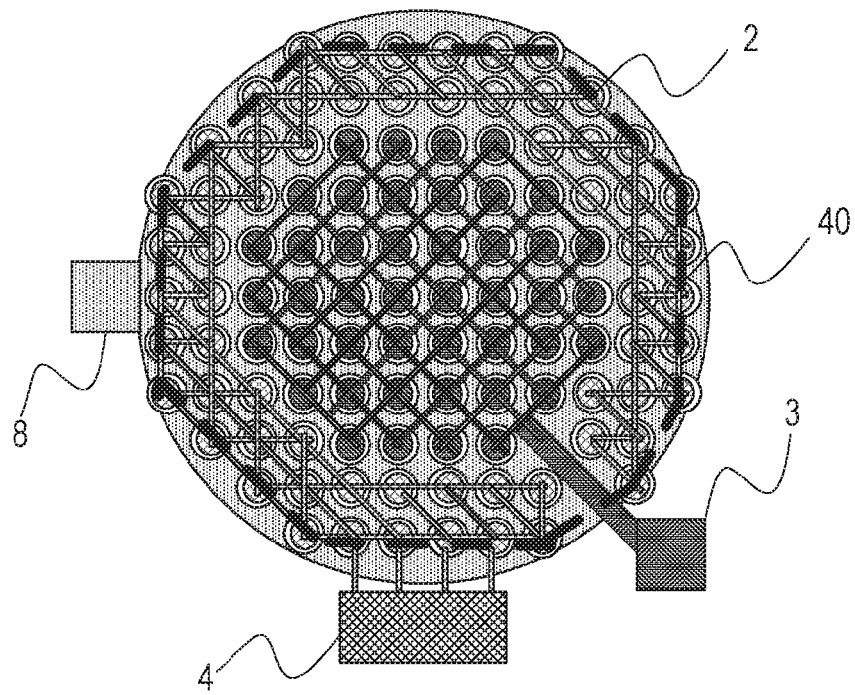
[Fig. 8]
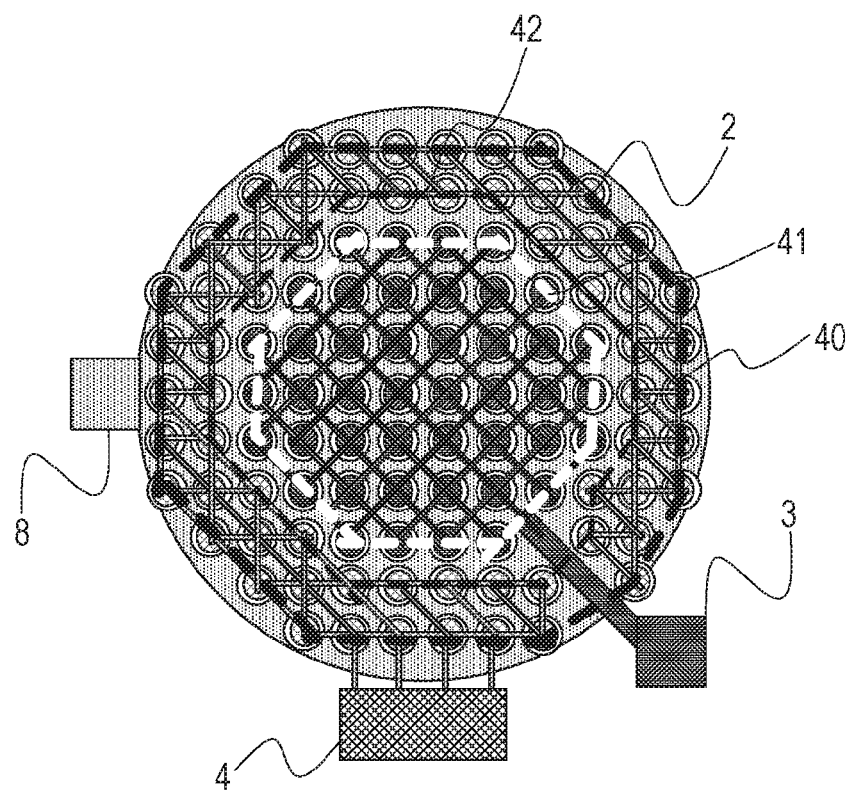

[Fig. 9]
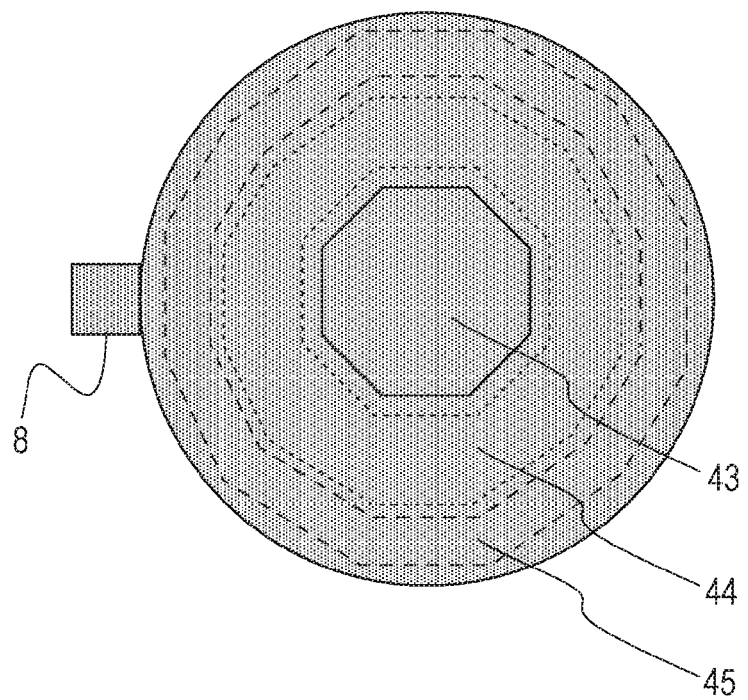
[Fig. 10]
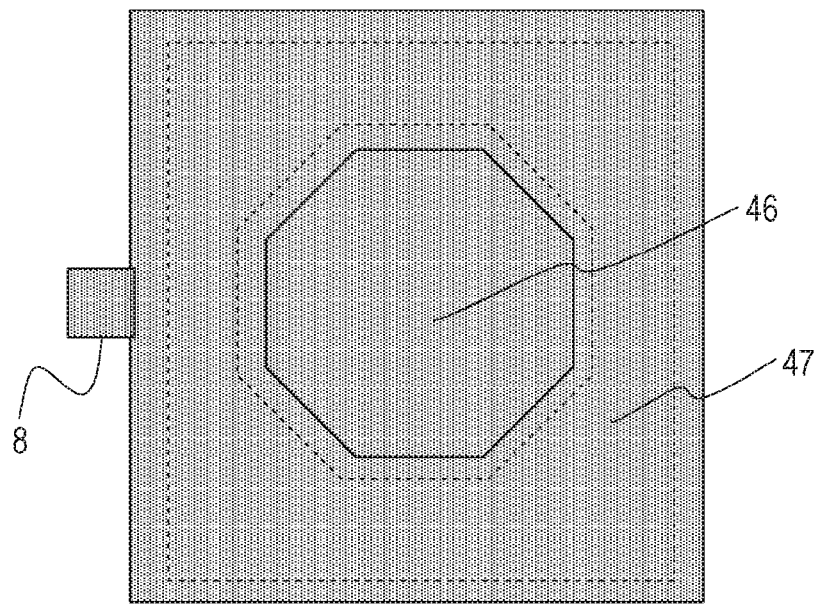

[Fig. 11]
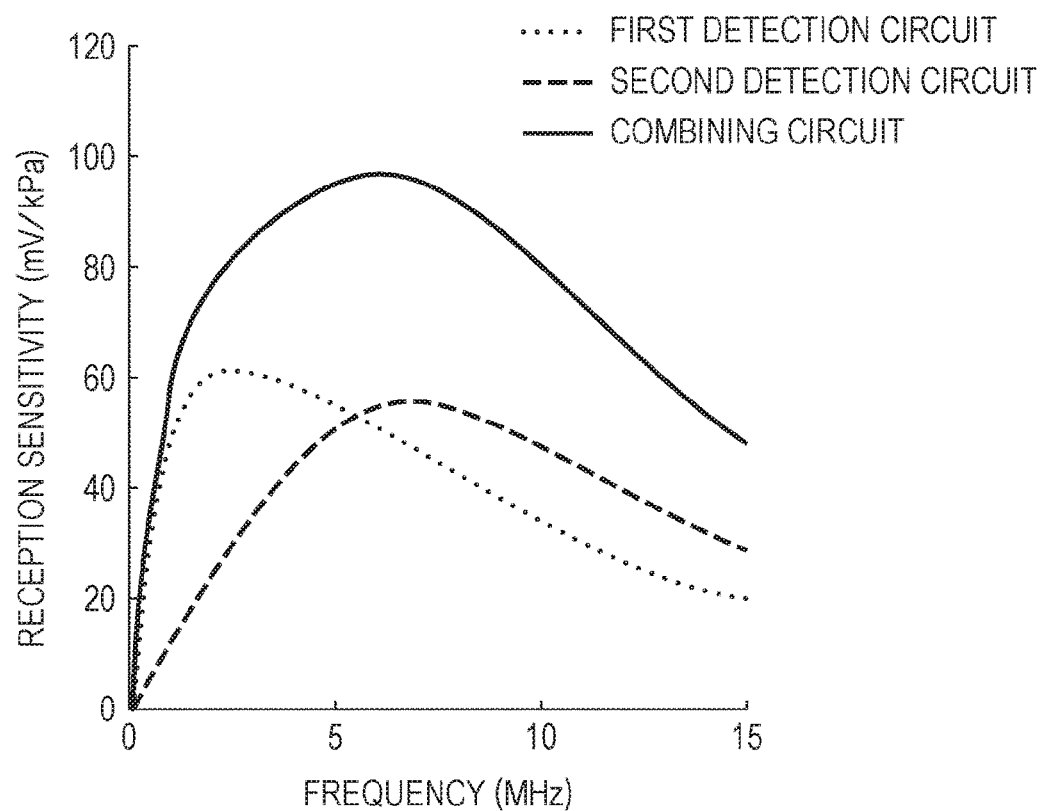
[Fig. 12]
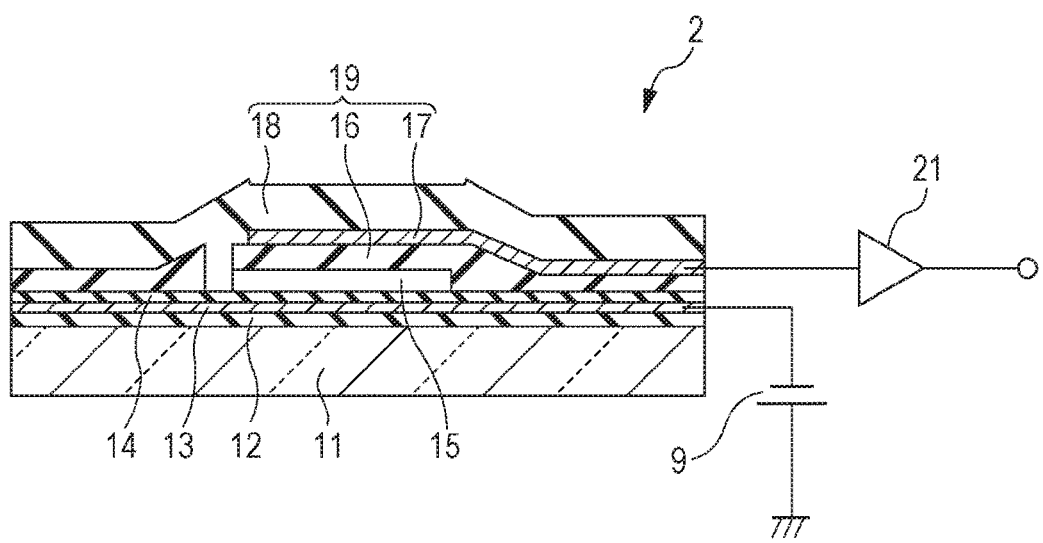

[Fig. 13]
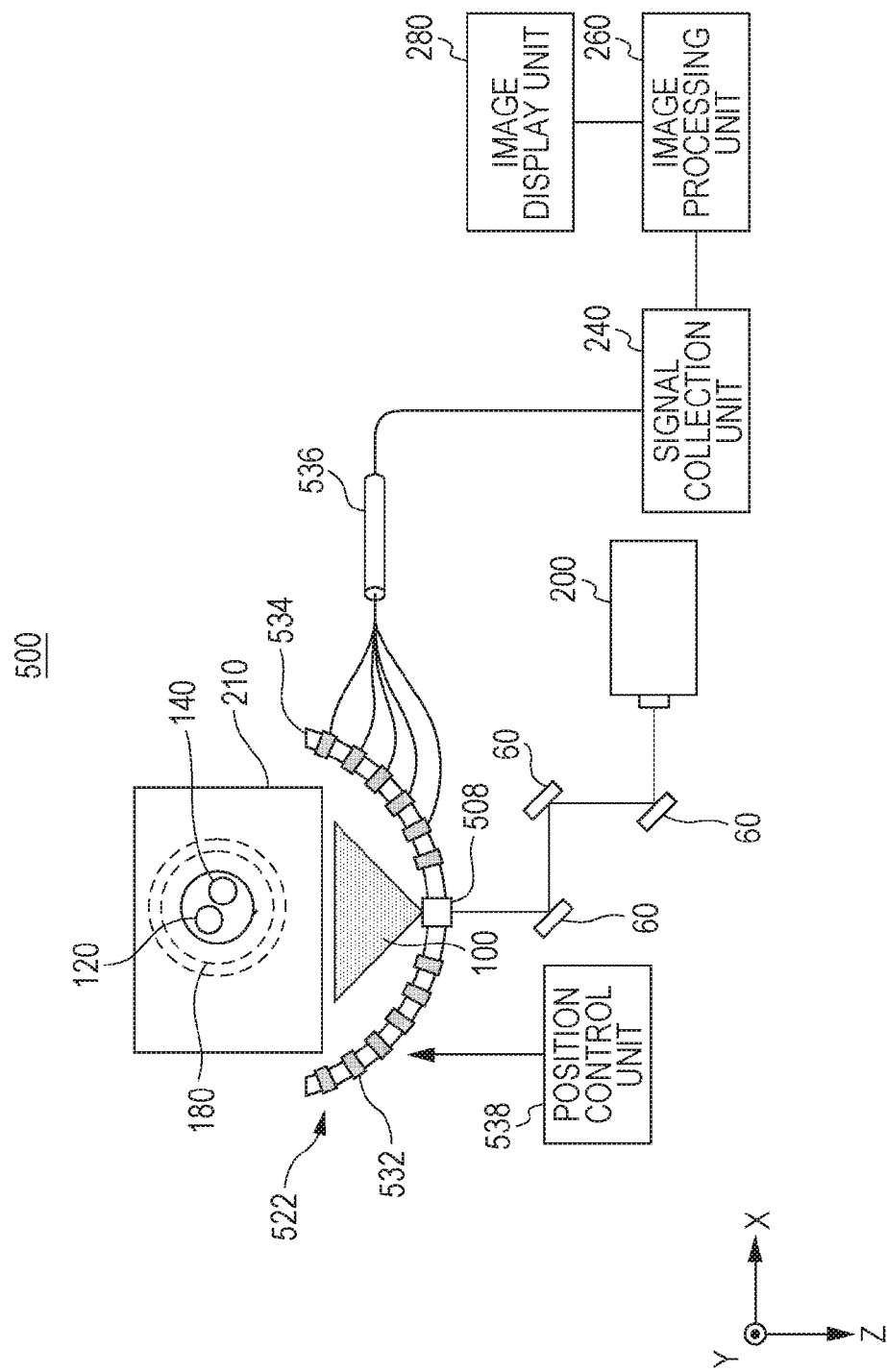

[Fig. 14]
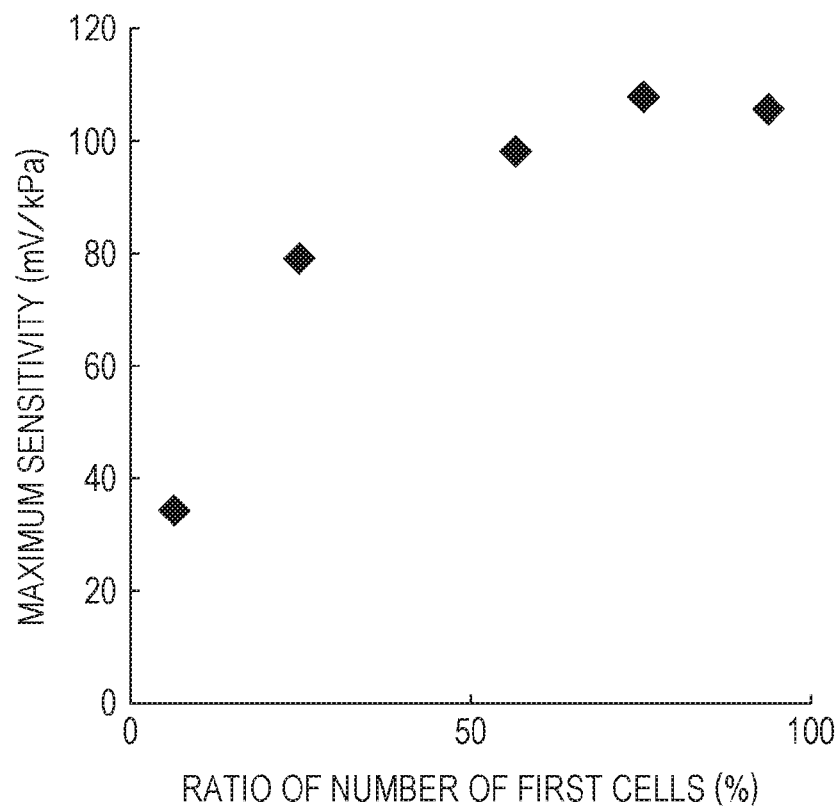
[Fig. 15]
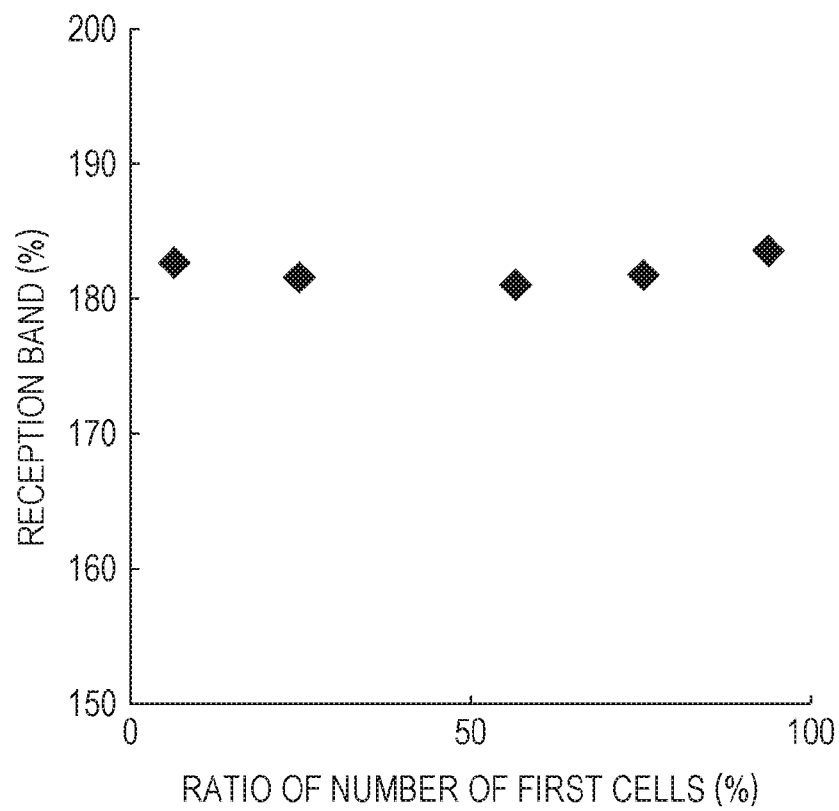

[Fig. 16]
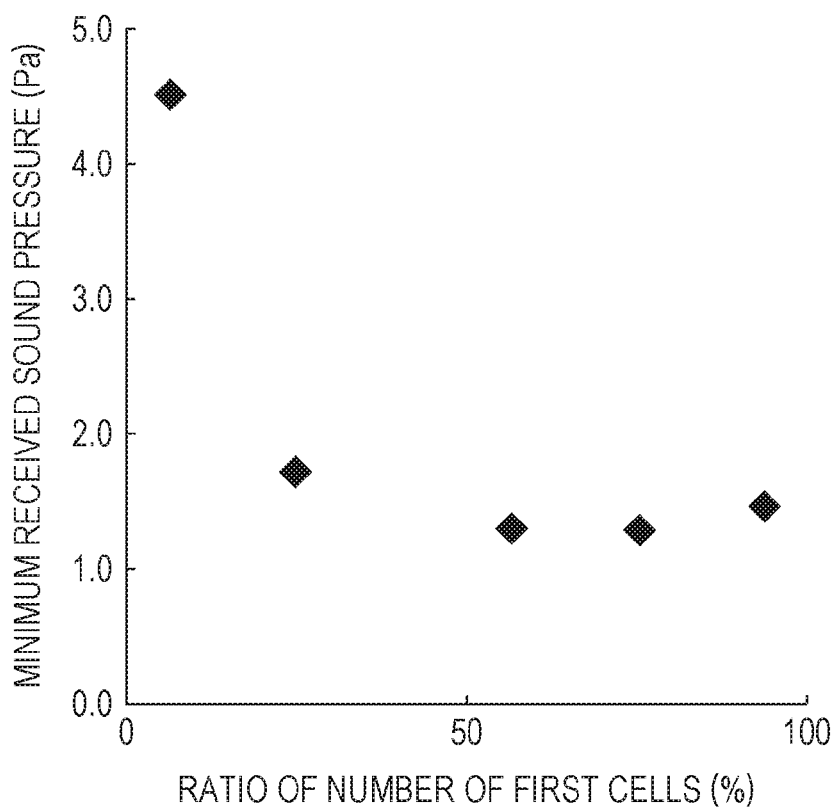
[Fig. 17]
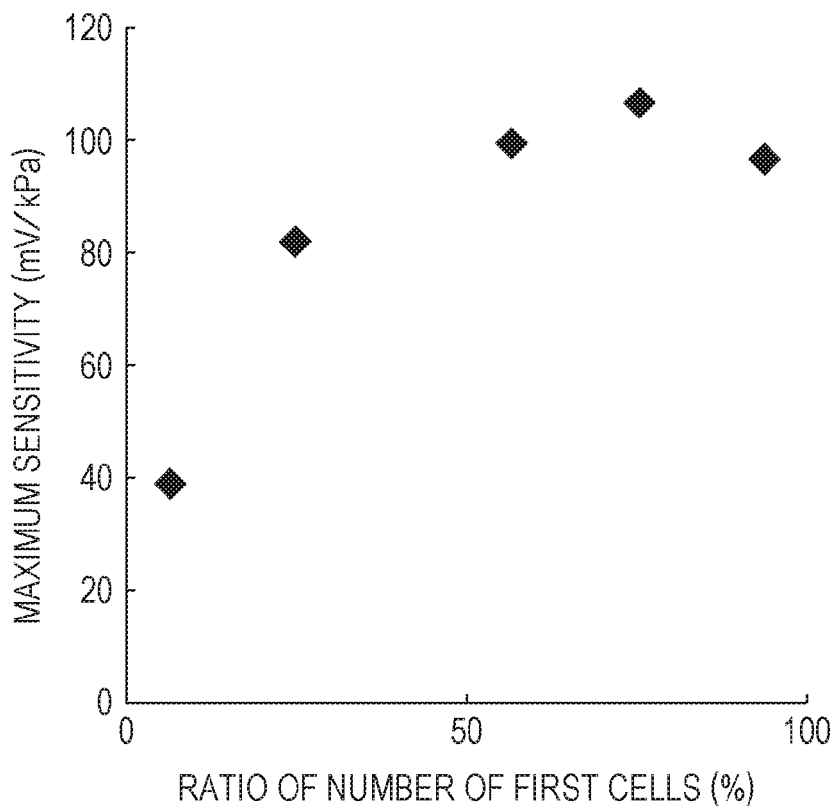

[Fig. 18]
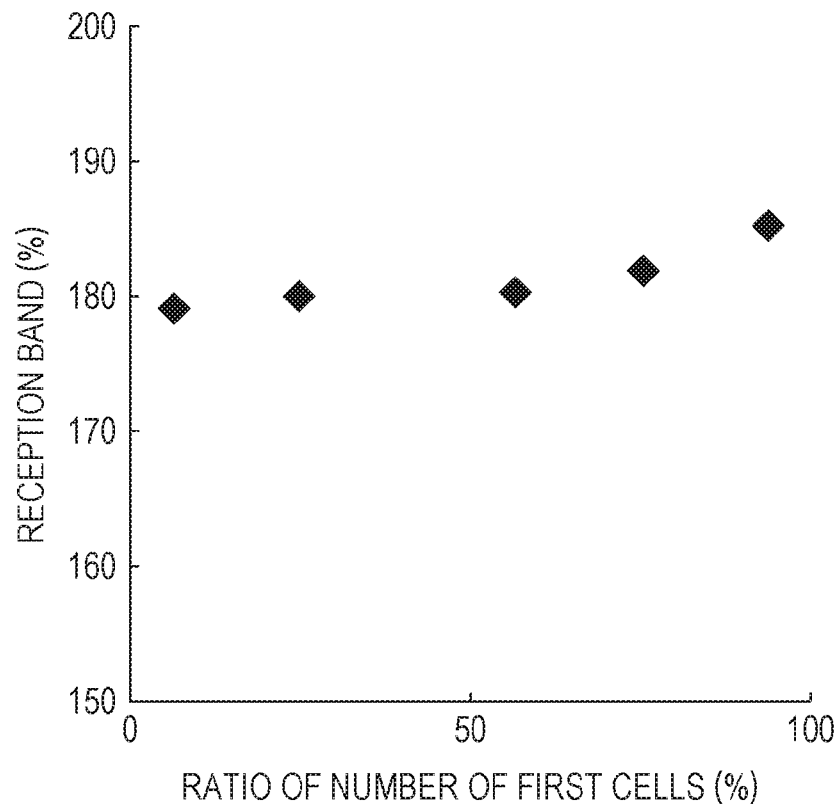
[Fig. 19]
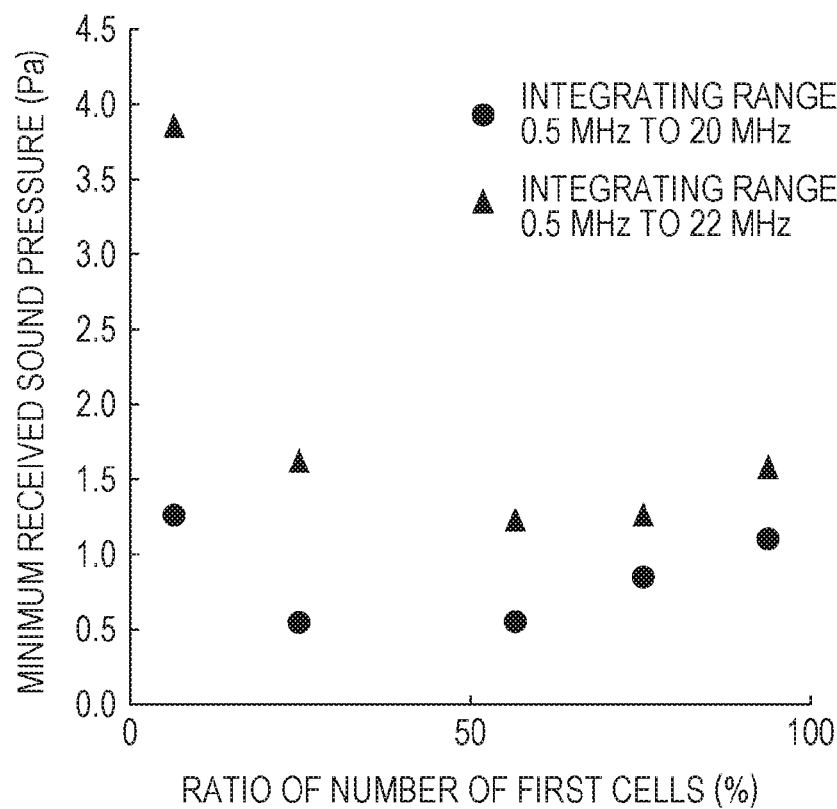

[Fig. 20A]
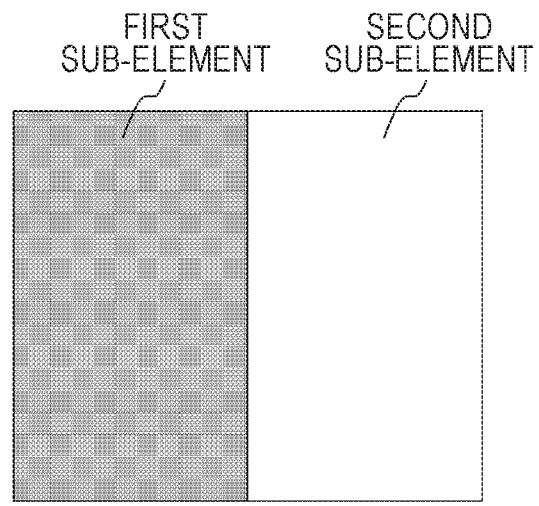
[Fig. 20B]
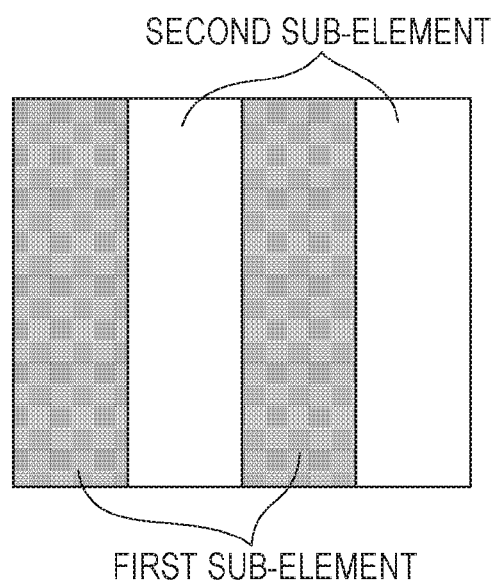
[Fig. 20C]
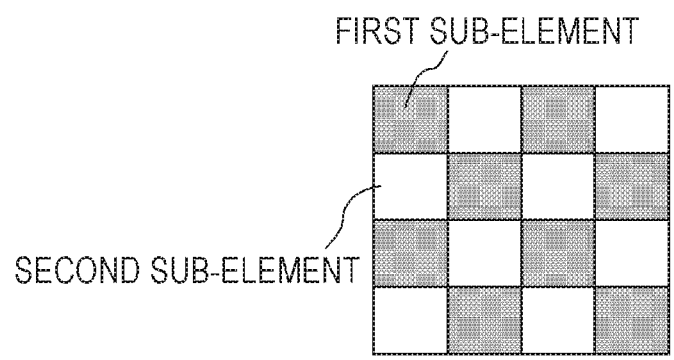

CAPACITIVE MICROMACHINED ULTRASONIC TRANSDUCER AND INFORMATION ACQUISITION APPARATUS INCLUDING CAPACITIVE MICROMACHINED ULTRASONIC TRANSDUCER

TECHNICAL FIELD

The present invention relates to a capacitive micromachined ultrasonic transducer and an information acquisition apparatus including the capacitive micromachined ultrasonic transducer, such as a photoacoustic apparatus.

BACKGROUND ART

Micro mechanical members produced using micro machining technology can perform a micrometer-scale machining operation, and a variety of micro functional elements have been developed using such micro mechanical members. Capacitive micromachined ultrasonic transducers (hereinafter also simply referred to as "CMUTs") using such technology have been researched to replace piezoelectric elements. Such capacitive micromachined ultrasonic transducer can send and receive an ultrasonic wave using vibration of a vibrating membrane and provide wide frequency characteristics in, in particular, liquid.

As one of such technologies, a capacitive micromachined ultrasonic transducer that provides wideband characteristics is described in PTL 1. The capacitive micro-machined ultrasonic transducer includes a plurality of cells each having a vibrating membrane with a high spring constant and a plurality of cells each having a vibrating membrane with a low spring constant.

CITATION LIST

Patent Literature

PTL 1: U.S. Pat. No. 5,870,351

SUMMARY OF INVENTION

According to a capacitive micromachined ultrasonic transducer that provides wideband characteristics by including a plurality of cells each having a vibrating membrane with a high spring constant and a plurality of cells each having a vibrating membrane with a low spring constant, by applying a common voltage from a common electrode, transmission and reception operations can be performed. In such a case, the conversion efficiency from vibration of the vibrating membrane into an electric signal in reception or from an electric signal into vibration of the vibrating membrane in transmission differs between the cell having the vibrating membrane with high spring constant and the cell having the vibrating membrane with low spring constant. Accordingly, although the capacitive micromachined ultrasonic transducer can provide the wideband characteristics, the conversion efficiency of the cell having the vibrating membrane with high spring constant differs from that of the cell having the vibrating membrane with low spring constant. As a result, the sensitivity may be limited to the lower conversion efficiency and, thus, the transmission sensitivity or the reception sensitivity may decrease.

Solution to Problem

According to an aspect of the present invention, a capacitive micromachined ultrasonic transducer includes an element including a first sub-element and a second sub-element. The first sub-element includes at least one first cell having a first vibrating membrane that includes one of two electrodes formed with a spacing therebetween and that is vibratably supported, and the second sub-element includes at least one second cell having a second vibrating membrane that includes one of two electrodes formed with a spacing therebetween and that is vibratably supported. The capacitive micro-machined ultrasonic transducer further includes a first detection circuit capable of detecting a signal generated by a change in capacitance between the two electrodes of the first cell caused by displacement of the first vibrating membrane, a second detection circuit capable of detecting a signal generated by a change in capacitance between the two electrodes of the second cell caused by displacement of the second vibrating membrane, and a combining circuit configured to combine the signals from the first detection circuit and the second detection circuit. The first sub-element is electrically connected to the first detection circuit, and the second sub-element is electrically connected to the second detection circuit. The first detection circuit and the second detection circuit have different cut-off frequencies.

Advantageous Effects of Invention

According to the present invention, the element including a plurality of cells is functionally divided into a plurality of sub-elements. Each of the sub-elements is connected to one of different detection circuits to acquire a signal. By combining the acquired signals, a signal for one element is obtained. In this manner, a wide reception band can be provided, without decreasing the reception sensitivity.

Further features of the present invention will become apparent from the following description of exemplary embodiments with reference to the attached drawings.

BRIEF DESCRIPTION OF DRAWINGS

FIG. 1 is a top view of an example of a CMUT according to an embodiment of the present invention.

FIG. 2 illustrates an example of the reception sensitivity of the CMUT according to the embodiment of the present invention.

FIG. 3 illustrates an example of the reception sensitivity of the CMUT according to the embodiment of the present invention.

FIG. 4 illustrates the output current of the CMUT according to the embodiment of the present invention.

FIG. 5 illustrates the current-to-voltage conversion gain of the CMUT according to the embodiment of the present invention.

FIG. 6 illustrates an example of a transimpedance circuit of the CMUT according to the embodiment of the present invention.

FIG. 7 illustrates an example of an element of the CMUT according to the embodiment of the present invention.

FIG. 8 illustrates an example of an element of the CMUT according to the embodiment of the present invention.

FIG. 9 illustrates an example of an element of the CMUT according to the embodiment of the present invention.

FIG. 10 illustrates an example of an element of the CMUT according to the embodiment of the present invention.

FIG. 11 illustrates an example of the reception sensitivity of a CMUT according to the embodiment of the present invention.

FIG. 12 is the cross-sectional view of an example of a cell of the CMUT according to the embodiment of the present invention.

FIG. 13 illustrates an example of a photoacoustic apparatus according to the embodiment of the present invention.

FIG. 14 illustrates the reception sensitivity of a CMUT according to EXAMPLE 1 of the present invention.

FIG. 15 illustrates the reception band of the CMUT according to EXAMPLE 1 of the present invention, FIG. 16 illustrates the minimum received sound pressure of the CMUT according to EXAMPLE 1 of the present invention.

FIG. 17 illustrates the reception sensitivity of a CMUT according to EXAMPLE 2 of the present invention.

FIG. 18 illustrates the reception band of the CMUT according to EXAMPLE 2 of the present invention.

FIG. 19 illustrates the minimum received sound pressure of the CMUT according to EXAMPLE 2 of the present invention.

FIG. 20A is a top view illustrating an example of an arrangement of a plurality of sub-elements.

FIG. 20B is a top view illustrating an example of an arrangement of a plurality of sub-elements.

FIG. 20C is a top view illustrating an example of an arrangement of a plurality of sub-elements.

DESCRIPTION OF EMBODIMENTS

According to an aspect of an embodiment of the present invention, a capactive micromachined ultrasonic transducer is characterized in that it includes an element including a first sub-element and a second sub-element is provided, and each of the first and second sub-elements includes a cell having a structure in which a vibrating membrane including one of two electrodes formed with a spacing therebetween is vibratably supported. The capacitive micromachined ultrasonic transducer further includes first and second detection circuits, each capable of detecting a signal generated by a change in capacitance between the two electrodes of the cell, and a combining circuit that combines the signals from the first and second detection circuits. In addition, the cut-off frequency of the first detection circuit differs from the cut-off frequency of the second detection circuit. By appropriately combining a plurality of sub-elements and detection circuits having different cut-off frequencies and combining signals output from different pairs each consisting of a sub-element and a detection circuit, a wide reception band is provided. In addition to embodiments and examples described below, capacitive micromachined ultrasonic transducers of a variety of configurations can be provided to meet the above-described configuration conditions. For example, as illustrated in FIG. 20A, a plurality of sub-elements are disposed in separate areas. Alternatively, as illustrated in FIG. 20B, a plurality of sub-elements are disposed in areas with alternately repetitive pattern. Still alternatively, as illustrated in FIG. 20C, a plurality of sub-elements are disposed in areas with a checkered pattern. The areas in which the sub-elements are disposed may be put together into one area or may be different areas. In the configuration, the plurality of detection circuits have different cut-off frequencies (any difference between the cut-off frequencies and any combination of the detection circuit and the cut-off frequency are allowed). Note that it is desirable that deviation of reception positions of the sub-elements from one another be minimized in the entire area of the sub-elements when an acoustic wave is received. Accordingly, it is desirable that the areas of the plurality of sub-elements be at least partially superimposed onto one another (e.g., in an alternately repetitive pattern, a reticular pattern, or a concentric circular ring pattern), instead of the pattern of sub-element areas illustrated in FIG. 20A in which the areas are clearly separate.

Embodiments of the present invention are described in detail below with reference to the accompanying drawings. Basically, the same numbering is used for similar components, and description of the same component is not repeated or is simplified. Note that detailed calculating formulae and calculation procedures described below should be appropriately changed in accordance with the configuration of apparatuses of the present invention and a variety of conditions. Therefore, the scope of the invention should not be construed as being limited by the following description.

A capacitive micromachined ultrasonic transducer (CMUT) according to an embodiment of the present invention is described below with reference to FIGS. 1 and 2. According to the present embodiment, a capacitive micromachined ultrasonic transducer 1 includes two sub-elements. In a first sub-element in dark grey, each of a plurality of cells that constitute the first sub-element includes a second electrode 17 (refer to FIG. 12). The second electrodes are connected to one another and are connected to a first detection circuit 5 via an electrode pad 3. In addition, in a second sub-element in light grey, each of a plurality of cells includes a second electrode 17. The second electrodes 17 are connected to one another and are connected to a second detection circuit 6 via an electrode pad. 4. The first detection circuit 5 and the second detection circuit 6 have different cut-off frequencies. The first detection circuit 5 and the second detection circuit 6 are connected to a combining circuit 7. Each of cells 2 that constitute the two sub-elements includes a first electrode 13 (refer to FIG. 12). The first electrodes 13 are connected to one another and are connected to a voltage applying unit 9 via an electrode pad 8. The number of the sub-elements is not limited to two, but may be three or more. Any desired number of the sub-elements can be employed. In addition, the number of the detection circuits can be increased in accordance with the number of the sub-elements, and the detection circuits of the sub-elements can have different cut-off frequencies. According to the present embodiment, the sub-elements are arranged in a pattern of concentric circular rings or concentric polygonal rings. Herein, the concentric circular rings are not limited to concentric perfectly circular rings, but may be concentric substantially circular rings.

To receive an acoustic wave, such as an ultrasonic wave, using the capacitive micro-machined ultrasonic transducer, a DC voltage is applied to the first electrode 13 by the voltage applying unit 9 so that a potential difference occurs between the first electrode 13 and the second electrode 17. Note that it is desirable that a negative voltage be applied to the first electrode 13. Upon receiving, for example, an ultrasonic wave, a vibrating membrane 119 having the second electrode 17 (refer to FIG. 12) deflects. Thus, a gap between the second electrode 17 and the first electrode 13 (the distance therebetween in the depth direction of a cavity 15 (refer to FIG. 12)) varies due to the deflection, resulting in a change in the electrostatic capacitance. The variation of the electrostatic capacitance produces an electric current flowing in the second electrode 17. An output current generated by the cells 2 that constitute the first sub-element is amplified by the first detection circuit 5 electrically connected to the cells 2 and is converted into a voltage signal. In contrast, an output current generated by the cells 2 that constitute the second sub-element is amplified by the second detection circuit 6 electrically connected to the cells 2 and is converted into a voltage signal. The two voltage signals generated by the detection circuits 5 and 6 through amplification and conversion of the output currents are combined into a voltage signal of one element by the combining circuit 7. Thus, the ultrasonic wave, for example, can be retrieved in the form of an electric signal.

FIG. 2 illustrates an example of the frequency characteristics of the reception sensitivity of the capacitive micromachined ultrasonic transducer according to the present embodiment. The frequency characteristics are measured for a voltage signal obtained by amplifying the output current generated upon reception of, for example, an ultrasonic wave and converting the output current into the corresponding voltage using the detection circuit. The ordinate is normalized using the peak value of the reception sensitivity. The cut-off frequency of the first detection circuit (indicated as a fine dotted line) having the first sub-element connected thereto (the frequency at a level of about −3 dB) is 12 MHz. The cut-off frequency of the second detection circuit (indicated as a rough dotted line) having the second sub-element connected thereto is 1 MHz. A signal obtained by combining the signal of the first detection circuit and the signal of the second detection circuit serves as a signal of the element (indicated as a solid line). As can be seen from comparison of the frequencies at a level of −6 dB, the lower frequency (Fmin) is 2.4 MHz, and the higher frequency (Fmax) is 15.6 MHz in the first detection circuit. In contrast, the lower frequency (Fmin) is 0.5 MHz, and the higher frequency (Fmax) is 11.2 MHz in the second detection circuit. When the two signals are combined, the lower frequency (Fmin) is 0.8 MHz, and the higher frequency (Fmax) is 15.4 MHz. Thus, very wideband characteristics can be obtained.

The constituent elements of the present embodiment are described in detail below.

Transimpedance Circuit

FIG. 6 illustrates a transimpedance circuit. The transimpedance circuit includes an operational amplifier 32, feedback resisters 33 and 35, and feedback capacitors 34 and 36. The operational amplifier 32 is connected to a positive and negative power supply (VDD, VSS). An inverting input terminal (−IN) is connected to the second electrode of the capacitive micromachined ultrasonic transducer 1. An output terminal (OUT) is connected to the inverting input terminal (−IN) via the feedback resister 33 and the feedback capacitor 34 connected in parallel so that the output signal is fed back. A non-inverting input terminal (+IN) is connected to a ground terminal (GND) via the feedback resister 35 and the feedback capacitor 36 connected in parallel. The voltage of the ground terminal is the midpoint potential between the positive power supply VDD and the negative power supply VSS. The resistance values of the feedback resisters 33 and 35 are the same, and the capacitance values of the feedback capacitors 34 and 36 are the same. Accordingly, it is desirable that there be no offset of the voltage. However, this is not a mandatory condition. According to the present embodiment, the setting values of the feedback resister 33 and the feedback capacitor 34 are one of the important factors, Shape of Element and Shape of Sub-Element According to the present embodiment, the shape of the element is not limited to one particular shape. For example, the shape may be circular or polygonal. The term "circular" as used herein is not to be understood to require a perfect circle, but may be substantially circular. Examples of the polygonal shape include a rectangular shape, a hexagonal shape, and an octagonal shape. It is desirable that the shape of the element be substantially circular. In general, an acoustic wave to be detected is coming to the element from all around. Accordingly, it is desirable that the directivity of the element that receives the acoustic wave have wide coverage. Thus, a substantially circular element having a wider directivity is more preferable than a polygonal element. Note that as illustrated in FIG. 7, the above-described substantially circular shape is formed by eight or more sides of a polygon formed from a line 40. The line 40 connects the centers of the cells disposed in the outermost peripheral portion among the cells that constitute the element.

The shape of a sub-element according to the present embodiment is appropriately selected in accordance with the above-described problems. It is desirable that the sub-elements be arranged in a pattern of concentric circular rings and the first sub-element be disposed inside the second sub-element. For example, as illustrated in FIG. 8, the outer shape of the element is circular. In contrast, a line 41 that connects the centers of the cells disposed in the outermost peripheral portion of the first sub-element forms an octagonal shape. In addition, in terms of the shape of the second sub-element, the line 40 that connects the centers of the cells disposed in the outermost peripheral portion forms a substantially circular shape. In addition, a line 42 that connects the centers of the cells disposed in the innermost peripheral portion also forms a substantially circular shape. The second sub-element is shaped with a center section missing. FIG. 9 illustrates an example of the shapes of the sub-elements with the cells, the electrode pads, and the detection circuit removed. The element illustrated in FIG. 9 includes three sub-elements, that is, a first sub-element 43, a second sub-element 44, and a third sub-element 45. The first sub-element 43 has a substantially circular shape formed from eight sides. The second sub-element 44 is shaped with a center section missing and has a substantially circular shape formed from eight side on a side adjacent to the first sub-element and a substantially circular shape formed from twelve sides on a side adjacent to the third sub-element. The third sub-element 45 is shaped with the center section missing. The third sub-element 45 has a substantially circular shape formed from twelve sides on a side adjacent to the second sub-element and also has a substantially circular shape formed from twelve sides on the outermost periphery. The number of the sub-elements can be set to a desired number, and the number of the sides can be set to a desired number.

As illustrated in FIG. 10, an element may have a rectangular shape. A first sub-element 46 may have a substantially circular shape formed from eight sides. A second sub-element 47 may be shaped with a center section missing. The second sub-element 47 may have a substantially circular shape formed from eight sides on the side adjacent to the first sub-element and a rectangular shape on the outermost periphery. To improve the directivity, it is desirable that the shape of the sub-element connected to a detection circuit having a high cut-off frequency be circular. High-frequency acoustic waves have a narrow directivity and tend to travel in a straight line. Accordingly, the intensity of sound is highest at the center of the receiving surface and its vicinity. In contrast, low-frequency acoustic waves have a wide directivity and are radially spread out, so that the difference between the intensities of the acoustic wave received at any two points on the receiving surface is small. Consequently, in the example illustrated in FIG. 10, by detecting a high-frequency acoustic wave at the center of the receiving surface and its vicinity at which the first sub-element connected to the detection circuit having a high cut-off frequency is disposed, the detection efficiency can be increased. That is, by disposing the first sub-element to which the detection circuit having a high cut-off frequency is connected in the center area which a high-frequency acoustic wave tends to reach, detection of a high-frequency acoustic wave can be facilitated. In addition, by disposing the second sub-element to which the detection circuit having a low cut-off frequency is connected in the peripheral area which a low-frequency acoustic wave also reach, detection of a low-frequency acoustic wave can be facilitated. By employing such a structure, low-frequency to high-frequency acoustic waves can be efficiently detected.

Cut-Off Frequency

According to the present embodiment, the term "cut-off frequency" of the detection circuit refers to a lowpass cut-off frequency at which the gain begins to decrease as the frequency increases beyond the cut-off frequency. It is desirable that the cut-off frequencies of the detection circuits connected to the sub-elements be selected so that a wide reception band of the CMUT can be provided. Assignment of cut-off frequencies to the sub-elements can be appropriately changed in accordance with an object to be measured and the performance of the desired reception band.

Note that according to the present embodiment, the cut-off frequency is appropriately determined in accordance with, for example, an object to be measured. For example, it is desirable that the cut-off frequency of a detection circuit having a low cut-off frequency be in the range from 0.1 MHz to 10 MHz and is more desirable that the cut-off frequency be in the range from 0.1 MHz to 5 MHz. In contrast, it is desirable that the cut-off frequency of a detection circuit having a high cut-off frequency be in the range from 2 MHz to 20 MHz and is more desirable that the cut-off frequency be in the range from 2 MHz to 15 MHz. That is, to detect a photoacoustic wave, it is important that a wide band from a low frequency to a high frequency can be detected, and it is desirable that the low frequency be 0.1 MHz. Also, since attenuation of the acoustic wave increases at a high frequency (about 20 MHz or higher), it is desirable that the above-described cut-off frequency range be employed from the viewpoint of attenuation.

Reception Band of CMUT

The reception band of a widely used CMUT is described below with reference to FIGS. 3, 4, and 5. FIG. 3 illustrates the reception band characteristics (the reception sensitivity) of a CMUT. FIG. 4 illustrates the output current characteristics of the CMUT. FIG. 5 illustrates the current-to-voltage conversion gain characteristics of the detection circuit. The reception band (the reception sensitivity) of a CMUT is determined by the product of the output current characteristics of the CMUT and the gain characteristics of the detection circuit. A transimpedance (current-to-voltage) amplifier circuit is used as the detection circuit.

If an electrostatic capacitance change is approximated by using the plane-parallel approximation, an output current I of the CMUT is given as follows:

$$I = P/((Zm+Zr)/(\varepsilon S^* Vb/d^2) + j\omega C) \quad (1)$$

$$Zm = j^*km^*((\omega/\omega_0^2) - 1/\omega) \quad (2)$$

where P is the pressure of the acoustic wave, $\varepsilon$ is the permittivity of vacuum, S is the area of the second electrode, Vb is a bias voltage applied between the two electrodes, d is the gap between the two electrodes, Zm is the mechanical impedance of the vibrating membrane, and Zr is the acoustic impedance of a medium. In addition, $\omega$ is the angular frequency of the acoustic wave, C is the total electrostatic capacitance, km is the spring constant of the vibrating membrane, $\omega_0$ is the resonance frequency, and j is the imaginary unit. In Equation (1), since the total electrostatic capacitance C is relatively small, the mechanical impedance Zm of the vibrating membrane is the function of the frequency. Furthermore, in general, the CMUT is used with the surface thereof in contact with liquid or gel. Since the acoustic impedance Zr of liquid is higher than the mechanical impedance Zm of the vibrating membrane, the acoustic impedance Zr has a large impact on the frequency characteristics of the output current illustrated in FIG. 4. The frequency at which the mechanical impedance Zm of the vibrating membrane becomes zero is the resonance frequency of the vibrating membrane. At that time, the output current illustrated in FIG. 4 is maximized. The peak frequency of the output current illustrated in FIG. 4 is 6 MHz.

The gain characteristics of the detection circuit illustrated in FIG. 5 are given using the following Equation (3), and the cut-off frequency of the detection circuit is given using the following Expression (4):

$$G = Rf/(1 + j\omega Rf^* Cf) \quad (3)$$

[Math. 1]

$$f \cong 1/(2\pi Rf^* Cf) \quad (4)$$

where G is the circuit gain, Rf is the feedback resistance, Cf is the feedback capacitance, $\omega$ is the angular frequency of the input current, and f is the cut-off frequency.

In addition, to stably drive the circuit illustrated in FIG. 6, the following expression needs to be satisfied:

[Math. 2]

$$Cf \gtrsim ((Cin)/(\pi^* GBW^* Rf))^{0.5} \quad (5)$$

where GBW is the gain-bandwidth product of the operational amplifier (amplifier gain 0 dB (=1)×frequency), and Cin is the capacitance parasitic on the inverting input terminal (−IN) of the operational amplifier. In general, if Cin is large, the operation performed by the operational amplifier is delayed, resulting in the negative feedback circuit being unstable. Accordingly, the circuit oscillates, and current-to-voltage conversion is unavailable. Therefore, GBW, Rf, and Cf suitable for Cin need to be selected, For example, to change the frequency characteristics of the CMUT illustrated in FIG. 3 towards lower frequencies, the resonance frequency of the output current illustrated in FIG. 4 can be shifted towards lower frequencies. Alternatively, the gain characteristics of the detection circuit illustrated in FIG. 5 can be shifted towards lower frequencies. To shift the cut-off frequency for the output current illustrated in FIG. 4 towards lower frequencies, the vibrating membrane of a cell can be made more flexible, and the spring constant can be decreased. However, if the flexibility of the vibrating membrane of the cell is too high, the voltage applicable to the electrode becomes too low. Thus, the voltage signal obtained on reception of an acoustic wave is too low. In addition, the deflection of the vibrating membrane increases and, thus, it is difficult to reduce the gap between the electrodes in order to increase the sensitivity. Accordingly, a certain level of stiffness of the vibrating membrane is required (Equations (1) and (2)). As a result, it is more desirable that the cut-off frequency of the gain characteristic of the detection circuit illustrated in FIG. 5 be shifted towards lower frequencies.

In contrast, to change the cut-off frequency of the voltage signal (the reception sensitivity) illustrated in FIG. 3 towards higher frequencies, the cut-off frequency of the output current illustrated in FIG. 4 can be shifted towards higher frequencies. Alternatively, the cut-off frequency of the gain characteristics of the detection circuit illustrated in FIG. 5 can be shifted towards higher frequencies. To shift the cut-off frequency for the output current illustrated in FIG. 4 towards higher frequencies, the spring constant can be increased by stiffening the vibrating membrane of the cell. However, if the stiffness of the vibrating membrane of the cell is too high, the voltage signal is too low on reception of an acoustic wave, since the spring constant is high. In addition, since the voltage applied to the electrodes increases, the dielectric strength voltage of the CMUT needs to be increased or the configuration of the apparatus needs to be changed (more specifically, for example, the power source needs to be changed, and the circuit and the apparatus needs to be changed to increase the dielectric strength voltage). As a result, there is a limit to the stiffness of the vibrating membrane (refer to Equations (1) and (2)). To increase the cut-off frequency of the gain characteristics of the detection circuit illustrated in FIG. 5, the feedback resistance Rf needs to be decreased so that the operational amplifier of the transimpedance circuit stably operates. If the feedback resistance Rf is decreased, the gain decreases. Consequently, the voltage signal obtained on reception of an acoustic wave disadvantageously decreases. Accordingly, it is desirable that both the cut-off frequency of the output current and the cut-off frequency of the gain characteristics of the detection circuit be shifted within the constraints of the two cut-off frequencies. If the configuration includes one output current (one element) and one detection circuit, usable wideband characteristics can be provided. However, there is a limit to an increase in the wideband characteristics.

According to the present embodiment, to make the reception sensitivity illustrated in FIG. 3 have wideband frequency characteristics, detection circuits having different cut-off frequencies are provided, and a plurality of cells are connected to each of the detection circuits. For example, when the resonance frequency of the output current of the first sub-element is set to 10 MHz and the cut-off frequency of the first detection circuit is set to 12 MHz, the frequency Fmin of the first sub-element at a reception sensitivity of −6 dB is 2.4 and the frequency Fmax is 15.6 MHz. In addition, when the resonance frequency of the output current of the second sub-element is set to 10 MHz and the cut-off frequency of the second detection circuit is 1 MHz, the frequency Fmin of the second sub-element at a reception sensitivity of −6 dB is 0.5 MHz, and the frequency Fmax is 11.2 MHz. After the reception sensitivities of the two sub-elements are combined, the frequency Fmin at a reception sensitivity of −6 dB is 0.8 MHz, and the frequency Fmax is 15.4 MHz. By combining the output signals obtained from a plurality of sub-elements to which detection circuits with different cut-off frequencies are connected, a very wideband frequency characteristics can be provided.

The output currents of the first sub-element and the second sub-element may have different resonance frequencies. The resonance frequency of the output current of a sub-element can be changed by changing spring constants of the cells that constitute a sub-element. In such a case, if the first electrode 13 (refer to FIG. 12) is common to the first and second sub-elements, the output current of the sub-element having a higher spring constant decreases, since the DC voltage applied to the first electrode 13 is limited by the sub-element having a lower spring constant (the more flexible sub-element). Accordingly, it is desirable that the first electrode 13 be provided to each of the sub-elements and the voltage applying unit be provided to each of the sub-elements. By employing such a configuration, an optimum DC voltage can be applied to each of the sub-elements. Thus, an acoustic wave can be detected with the output current being high. Note that if a plurality of voltage applying units are provided, the number of interconnection lines increases and, thus, the load imposed on a device and a circuit increases. In this respect, it is desirable that the spring constants of the cells that constitute the sub-elements be substantially the same and the first electrode 13 be common to the sub-elements.

First Electrode (Lower Electrode) of Cell

It is desirable that of the first electrode (the lower electrode) and the second electrode of each of the cells that constitute a sub-element, the electrode that is not connected to the detection circuit be selected as a common electrode and the DC voltage be applied to the common electrode. By employing a configuration in which a common DC voltage is applied to the common electrode, the number of interconnection lines can be reduced and, thus, the load imposed on a device and a circuit can be reduced.

Cell Structure

A first cell that constitutes the first sub-element nd a second cell that constitutes the second sub-element can have the same shape and can be made of the same material, in addition, the cells that constitute each of the sub-elements can have the same shape and can be made of the same material. By making the cells that constitute the element the same shape, the sensitivity is not limited by the sensitivity of the cell having low conversion efficiency among the cells that constitute the element. Accordingly, wideband reception characteristics can be obtained while ensuring high sensitivity. As used herein, the term "same" means either "exactly the same" or "substantially the same". If the sizes or the thicknesses of the vibrating membranes or the heights of the cavities of the cells that constitute the element are within the manufacturing variations, it can be said that the sizes, the thicknesses, or the heights are substantially the same. The same applies to the materials. It is desirable that the manufacturing variations be in the range from 0.5 times to 1.5 times the reference value.

Number of Cells of Element

Any number of cells that constitute an element can be employed. That is, the number of cells is not limited to that illustrated in FIG. 1. It is desirable that a number of cells capable of providing desired resolution and sensitivity be employed. In addition, any number of cells can be employed to constitute a sub-element. Note that it is desirable that if each of the peak frequencies of the output currents of the first sub-element and the second sub-element is between the cut-off frequencies of the first and second detection circuits, the number of cells of the first sub-element be greater than that of the second sub-element. It is more desirable that the number of cells of the first sub-element be in the range of 55% to 95% of the number of all the cells of the element. In addition, it is desirable that if each of the peak frequencies of the output currents of the first sub-element and the second sub-element is higher than each of the cut-off frequencies of the first and second detection circuits, the number of cells of the first sub-element be substantially the same as that of the second sub-element. It is more desirable that the number of cells of the first sub-element be in the range of 25% to 75% of the number of all the cells.

As can be seen from Equation (3), according to the gain characteristics of the detection circuit, the circuit gain increases with increasing feedback resistance Rf, resulting in the improved reception sensitivity. The following expression is derived from Expressions (4) and (5):

[Math. 3]

$$Cf \gtrsim ((Cin*2*f*Cf)/GBW) \qquad (6)$$

As can be seen from Expression (6), if a cut-off frequency f is increased, a feedback capacitance Cf needs to be increased to prevent oscillation of the detection circuit. Accordingly, the cut-off frequency have to be increased by decreasing the feedback resistance Rf. As a result, the cut-off frequency increases with decreasing circuit gain, and the reception sensitivity decreases.

In contrast, since in the detection circuit having a low cut-off frequency, the feedback capacitance Cf required to prevent the oscillation of the detection circuit is low, the circuit gain can be increased by increasing the feedback resistance Rf. In addition, even when the feedback resistance Rf is decreased by increasing the feedback capacitance Cf, a sufficient circuit gain can be obtained. Accordingly, the degree of design freedom is high. To obtain a wide reception band by combining the reception sensitivities of two sub-elements, it is desirable that the magnitude of the reception sensitivity of one of the two sub-elements be substantially the same as that of the other sub-element, as illustrated in FIG. 11. As used herein, the term "substantially the same magnitudes" means that the ratio of the peak value of the magnitude of the reception sensitivity of one of the two sub-elements to that of the other is 0.5 or greater and 0.9 or less. It is more desirable that the ratio of the peak value of one of the reception sensitivities to that of the other be 0.7 or greater and 0.9 or less. If one of the reception sensitivities is significantly greater than the other, the reception band is narrowed.

A method for obtaining wideband reception sensitivity illustrated in FIG. 11 is described below. The following description is given on the assumption that the peak frequencies of the output currents of the first and second sub-elements are between the cut-off frequencies of the first and second detection circuits. To maximize the combined reception sensitivity, it is desirable that the gain of the first detection circuit be maximized while preventing the oscillation of the detection circuit and, thereafter, the second detection circuit be controlled so as to have a wideband. In such a case, as described above, to increase the reception sensitivity of the first sub-element and, thus, increase the combined reception sensitivity, it is desirable that the number of cells that constitute the first sub-element be greater than the number of cells that constitute the second sub-element.

The following description is for the case in which each of the peak frequencies of the output currents of the first and second sub-elements is greater than the cut-off frequency of each of the first and second detection circuits. To maximize the combined reception sensitivity, it is desirable that the gain of the first detection circuit be maximized while preventing the oscillation of the detection circuit and, thereafter, the second detection circuit be controlled so as to have a wide band. In such a case, as described above, to increase the reception sensitivity of the first sub-element and increase the combined reception sensitivity, it is desirable that the number of cells that constitute the first sub-element be substantially the same as the number of cells that constitute the second sub-element. Note that any number of sub-elements that constitute the element can be employed. However, if the load imposed on a device and the detection circuit is taken into account, it is desirable that about two sub-elements be employed.

Cell

The structure of the cell that constitutes the element according to the present embodiment is described with reference to FIGS. 1 and 12. The structure of the cell 2 includes a substrate 11, a first insulating film 12 formed on the substrate 11, the first electrode 13 formed on the first insulating film 12, and a second insulating film 14 formed on the first electrode 13. In addition, the structure of the cell 2 includes the vibrating membrane 19 including a membrane 16, the second electrode 17, and a sealing film 18. The vibrating membrane 19 is disposed on the second insulating film 14 with the cavity 15, which serves as a gap, therebetween. If the substrate 11 is an electrically insulating substrate, such as a glass substrate, the need for the first insulating film 12 can be eliminated. As viewed from the top, the cavity 15 is circular in shape, and a portion that vibrates is circular in shape. However, the cavity 15 may be square or rectangular in shape. The structure of the cell 2 further includes the voltage applying unit 9 that applies a voltage between the first electrode 13 and the second electrode 17 of the cell 2 and a detection circuit 21 that amplifies an electric signal retrieved from the second electrode 17. The first electrode 13 faces the second electrode 17, and a bias voltage is applied between the first electrode 13 and the second electrode 17 by the voltage applying unit 9. The cell 2 can retrieve an electric signal from the second electrode 17.

According to the present embodiment, an electric signal is retrieved from the second electrode 17. However, the electric signal may be retrieved from the back side of the substrate 11 using, for example, through-wiring. In addition, according to the present embodiment, the first electrode 13 serves as a common electrode, and an electric signal is retrieved from the second electrode 17. However, a configuration that is the reverse of the above-described configuration may be employed. That is, the second electrode 17 may serve as the common electrode, and the first electrode 13 may serve as a lead-out electrode.

Principal of Driving Capacitive Micromachined Ultrasonic Transducer

When an acoustic wave, such as an ultrasonic wave, is received by the capacitive micromachined ultrasonic transducer according to the present embodiment, a DC voltage is applied to the first electrode 13 by the voltage applying unit 9 so that a potential difference occurs between the first electrode 13 and the second electrode 17. Upon receiving, for example, an ultrasonic wave, the vibrating membrane including the second electrode 17 deflects. Accordingly, the gap between the second electrode 17 and the first electrode 13 (the distance in the depth direction of the cavity 15) varies and, thus, the electrostatic capacitance changes. The change in the electrostatic capacitance produces an electric current flowing in the second electrode 17. An output current generated by the cells 2 that constitute the first sub-element is amplified by the first detection circuit 5 and is converted into a voltage. In contrast, an output current generated by the cells 2 that constitute the second sub-element is amplified by the second detection circuit 6 and is converted into a voltage. The two voltage signals obtained through amplification and conversion performed by the two detection circuits 5 and 6 are combined into the voltage signal of one element by the combining circuit 7. Thus, the acoustic wave can be retrieved in the form of an electric signal. As described above, by changing the configuration of the electrodes, the second electrode may be used as a common electrode, and a DC voltage may be applied to the second electrode. In addition, the first electrode may be divided for each of the sub-elements, and each of the divided electrodes may be connected to one of the detection circuits.

In addition, when an ultrasonic wave is transmitted, a DC voltage is applied to the first electrode (one of the electrodes), and an AC voltage is applied to the second electrode (the other electrode). Thus, the vibrating membrane 19 is vibrated by an electrostatic force. In this manner, an ultrasonic wave, for example, can be transmitted by the vibration. By changing the configuration of the electrodes, the second electrode may be used as a common electrode, and a DC voltage may be applied to the second electrode. In addition, the first electrode may be divided for each of the sub-elements, and an AC voltage may be applied to the divided first electrodes. Thus, the vibrating membrane may be vibrated.

The above-described electric signal of one element corresponds to one pixel, and the amplitude and phase information regarding an acoustic wave is averaged. In, for example, diagnosis devices including the capacitive micromachined ultrasonic transducer 1, the image of a test object (an object to be measured) is generated on the basis of the pixel-based amplitude and the phase information.

Photoacoustic Apparatus

FIG. 13 is a block diagram of a photoacoustic apparatus according to the present embodiment. The same reference numerals are used in FIG. 13 to describe those components that correspond to the components of FIG. 1, and descriptions of the components are not repeated unless otherwise necessary. A photoacoustic apparatus 500 according to the present embodiment (hereinafter simply referred to as an "apparatus 500") is characterized by the configuration of a probe 522. The probe 522 includes a plurality of transducers 532 and a holding member 534. Each of the transducers 532 is the CMUT according to the present embodiment. The holding member 534 is formed in a nearly spherical crown shape. The transducers 532 are held by the holding member 534 along the spherical crown shape. The transducers 532 are held so that the directions of the highest reception sensitivities of the transducers 532 converge to one point. According to the present embodiment, the directions of the highest reception sensitivities of the transducers 532 are headed toward an area including the center of curvature of the nearly spherical crown shape of the holding member 534. An output terminal of each of the transducers 532 for an analog electric signal is connected to a corresponding one of signal wiring lines. The analog electric signals output from the transducers 532 are combined by a signal wiring line 536 formed by commonly connecting the signal wiring lines. The combined signal is transmitted to a signal collection unit 240 via the signal wiring line 536. It should be noted that the configuration is not limited thereto. The analog electric signals output from the transducers 532 need not be combined by the signal wiring line 536 formed by commonly connecting the signal wiring lines. The analog electric signals may be independently transmitted in parallel to the signal collection unit 240.

A light emitting unit 508 is held in the middle of the holding member 534 in an integrated manner with the probe 522. The light emitting unit 508 emits a light beam 100 to a test object 210. According to the present embodiment, a light beam generated by a light source 200 capable of emitting (oscillating) a pulse of light is led to the light emitting unit 508 via a mirror 60. Thus, the light emitting unit 508 emits the light beam from the probe 522 (in −Z direction in FIG. 13). A drive device, that is, a position control unit 538 moves the probe 522. For example, the position control unit 538 may move the probe 522 in a spiral motion, and the light emitting unit 508 may emit the light beam 100 at any light-emitting position in the spiral trajectory along which the light emitting unit 508 moves due to the spiral motion. In such a case, the light emitting unit 508, which is integrated with the probe 522, may emit the light beam 100 at each of acoustic wave receiving positions (light emitting positions) in accordance with the spiral motion caused by the position control unit 538. The transducers 532 may receive an acoustic wave generated based on the emission, convert the acoustic wave into an analog electric signal, and transmit the analog electric signal to the signal collection unit 240. In this manner, when acoustic matching liquid is disposed between the probe 522 and the test object 210, acoustic noise caused by shaking of the acoustic matching liquid resulted from the motion of the probe 522 can be reduced. Note that the light source 200 is not limited to a light source that emits a pulse of light. The light source 200 may be a light source, such as a light emitting diode (LED), which emits continuous light.

When a light beam is incident upon the test object 210, absorbers 120 and 140 absorb the light beam and thermally expand, so that an acoustic wave 180 is generated. The probe 522 receives the acoustic wave 180. A received signal is sent to the signal collection unit 240 via the signal wiring line 536 and is subjected to image processing performed by an image processing unit 260. In this manner, the information regarding the inside of the test object can be acquired. The data subjected to image processing can be displayed by using an image display unit 280. The apparatus 500 may further include a circuit unit that sends and receives a signal between the transducer (i.e., the capacitive micromachined ultrasonic transducer) and the image processing unit 260 and a control unit that controls the image processing unit 260 and the circuit unit. In transmission and reception, the circuit unit is controlled by a system to switch between a transmission mode and a reception mode and perform beam forming.

More particular examples are described below.

EXAMPLE 1

According to EXAMPLE 1, a capacitive micromachined ultrasonic transducer including two sub-elements and two detection circuits is provided. The reception band of the capacitive micromachined ultrasonic transducer is described when the peak frequencies of the output currents of the two sub-elements are between the cut-off frequencies of the first and second detection circuits and when the ratio of the number of the cells that constitute each of the two sub-elements is changed.

The capacitive micromachined ultrasonic transducer according to EXAMPLE 1 is described first. An element of the capacitive micromachined ultrasonic transducer 1 has a substantially circular shape with a diameter of 2 mm. As illustrated in FIG. 8, the element includes two sub-elements. A cell is circular in shape, and the diameter of a cavity 15 is 36 μm. Neighboring cells are disposed with a spacing of 39 μm therebetween. Although not illustrated in FIG. 8, the number of all the cells actually disposed inside the element is 2400. As illustrated in FIG. 12, the cell 2 includes a silicon substrate 11 having a thickness of 300 μm, a first insulating film 12 formed on the silicon substrate 11, a first electrode 13 formed on the first insulating film 12, and a second insulating film 14 formed on the first electrode 13. The cell 2 further includes a vibrating membrane 19 including a second electrode 17, a membrane 16, and a sealing film 18 and a cavity 15. The cavity 15 is 150 nm in height. The cell 2 still further includes a voltage applying unit 9 that applies a bias voltage between the first electrode 13 and the second electrode 17 and a detection circuit 21.

The first insulating film 12 is a silicon dioxide film having a thickness of 1 μm and made using thermal oxidation. The second insulating film 14 is a silicon dioxide film having a thickness of 50 nm and made using plasma enhanced chemical vapor de-position (PE-CVD). The first electrode 13 is made of titanium and is 50 nm in thickness. The second electrode 17 is made of an aluminum alloy and is 100 nm in thickness. Each of the membrane 16 and the sealing film 18 is a silicon nitride film made using PE-CVD and a tensile stress of 450 MPa or less. The membrane 16 is 400 nm in thickness. The sealing film 18 is 850 nm in thickness. By using such cells and changing the ratio of the number of cells that constitute the first sub-element, the capacitive micromachined ultrasonic transducer illustrated in FIG. 1 is produced.

The cut-off frequency of the first detection circuit is 8 MHz, and the cut-off frequency of the second detection circuit is 1 MHz. The peak frequency of the output current of each of the two sub-elements is 7 MHz. The number of cells that constitute the element is 2400. The shapes of the cells are substantially the same within manufacturing variation. The ratio of the number of cells that constitute the first sub-element to the number of all the cells that constitute the element is changed to each of the following values: 94%, 75%, 57%, 25%, and 6%. The maximum values of the reception sensitivity for the ratios are illustrated in FIG. 14. In addition, the reception bands (the expanded amounts each expressed as a percent of an existing reception band) are illustrated in FIG. 15, and the minimum received sound pressures are illustrated in FIG. 16. As can be seen from FIG. 14, the reception sensitivity is maximized at a ratio of the number of cells of the first sub-element of 75% and its vicinity. Furthermore, as can be seen from FIG. 15, by employing the configuration according to EXAMPLE 1, the reception band is widened. Still furthermore, as can be seen from FIG. 16, the minimum received sound pressure is minimized at a ratio of the number of cells of the first sub-element of 75% and its vicinity. As used herein, the term "minimum received sound pressure" refers to the S/N when an acoustic wave is received. The minimum received sound pressure can be given using the following equation: minimum received sound pressure=$2^{0.5}$×integrating noise/maximum sensitivity. The integrating noise represents the integrating value of circuit noise generated when the CMUT is connected to the detection circuit. According to EXAMPLE 1, the integrating range is set to a range from 0.5 MHz to 20 MHz. Since a smaller acoustic wave can be detected with decreasing minimum received sound pressure, it is desirable to employ a configuration that decreases the minimum received sound pressure.

As described above, if the peak frequency of the output current of the cells that constitute the element is between the cut-off frequencies of the first and second detection circuits, it is desirable that the number of cells of the first sub-element be greater than that of the second sub-element. In addition, to detect an acoustic wave over a wide band with high sensitivity, it is desirable that the number of the cells of the first sub-element be in the range from 55% to 95% of the number of all the cells.

EXAMPLE 2

According to EXAMPLE 2, a capacitive micromachined ultrasonic transducer including two sub-elements and one detection circuit is provided. The reception band of the capacitive micromachined ultrasonic transducer is described when the peak frequency of the output current of the cells of each of the two sub-elements is greater than each of the cut-off frequencies of the first and second detection circuits and when the ratio of the number of cells that constitute one of the two sub-elements to that of the other sub-element is changed. The capacitive micromachined ultrasonic transducer according to EXAMPLE 2 can be produced in the same manner as in EXAMPLE 1. According to EXAMPLE 2, the sealing film 18 is 1550 nm in thickness.

The cut-off frequency of the first detection circuit is 8 MHz, and the cut-off frequency of the second detection circuit is 1 MHz. The peak frequency of the output current of the capacitive micromachined ultrasonic transducer is 14 MHz. The number of cells that constitute the element is 2400, and the shapes of the cells are substantially the same (within manufacturing variations). The ratio of the number of cells that constitute the first sub-element to the number of all the cells that constitute the element is changed to each of the following values: 94%, 75%, 57%, 25%, and 6%. The maximum values of the reception sensitivity for the ratios are illustrated in FIG. 17. In addition, the reception bands are illustrated in FIG. 18. The minimum received sound pressures are illustrated in FIG. 19, As can be seen from FIG. 17, the reception sensitivity is maximized at a ratio of the number of cells of the first sub-element of 75% and its vicinity. Furthermore, as can be seen from FIG. 18, by employing the configuration according to EXAMPLE 2, the reception band is widened. Still furthermore, as can be seen from FIG. 19, the minimum received sound pressure is minimized at a ratio of the number of cells of the first sub-element of 50% and its vicinity. According to EXAMPLE 2, the integrating ranges are set to a range from 0.5 MHz to 20 MHz and a range from 0.5 MHz to 22 MHz. If the integrating range of noise is changed, the minimum received sound pressure changes. Accordingly, it is desirable to employ a configuration that minimizes the minimum received sound pressure within the used frequency range.

As described above, if the peak frequency of the output current of the cells that constitute the element is higher than each of the cut-off frequencies of the first and second detection circuits, it is desirable that the number of cells of the first sub-element is substantially the same as that of the second sub-element. To detect an acoustic wave over a wide band with high sensitivity, it is desirable that the number of the cells of the first sub-element be in the range from 25% to 75% of the number of all the cells.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-209430, filed Oct. 24, 2015, which is hereby incorporated by reference herein in its entirety.

INDUSTRIAL APPLICABILITY

The present invention is applicable to, for example, photoacoustic apparatuses that acquire information regarding the inside of a biological body and existing ultrasonic diagnostic equipment. That is, by using an ultrasonic probe including a plurality of the capacitive micromachined ultrasonic transducers according to the present invention, a test object information acquisition apparatus that receives an acoustic wave from a test object and acquires the information regarding the test object can be provided. Examples of the information acquisition apparatus include ultrasonic diagnostic equipment including a light source that emits a light beam to a test object, an ultrasonic probe that detects an acoustic wave coming from the test object excited by emission of the light beam, and a signal processing unit that converts a detection signal into image information. The example further include ultrasonic diagnostic equipment including an ultrasonic probe that is capable of transmitting an acoustic wave to the test object and that includes a plurality of the capacitive micromachined ultrasonic transducers according to the present invention for detecting the ultrasonic wave reflected off the test object and a signal processing unit that converts a detection signal into image information. The signal processing unit processes a signal to form the image of the test object. Furthermore, the present invention is applicable to other uses, such as a supersonic flaw detector.

REFERENCE SIGNS LIST 1 capacitive micromachined ultrasonic transducer
2 cell (first cell, second cell)
5 first detection circuit
6 second detection circuit
7 combining circuit
13 first electrode
15 gap (cavity)
16 vibrating membrane (first vibrating membrane, second vibrating membrane)
17 second electrode

The invention claimed is:

1. A capacitive micromachined ultrasonic transducer comprising:
    an element including a first sub-element and a second sub-element, the first sub-element including a plurality of first cells, the second sub-element including a plurality of second cells, the first cell including a first electrode and a first membrane, the first membrane including a second electrode, there being a space between the first membrane and the first electrode, the first membrane being vibratably supported, and the second cell including a first electrode and a second membrane, the second membrane including a second electrode, there being a space between the second membrane and the first electrode, the second membrane being vibratably supported;
    a first detection circuit configured to generate a first signal generated by a change in capacitance between the first electrode and the second electrode of the first cell;
    a second detection circuit configured to generate a second signal generated by a change in capacitance between the first electrode and the second electrode of the second cell; and
    a combining circuit configured to combine the first signal and the second signal,
    wherein the first sub-element is electrically connected to the first detection circuit,
    wherein the second sub-element is electrically connected to the second detection circuit, and
    wherein the first detection circuit and the second detection circuit have different cut-off frequencies, and
    wherein the first sub-element and the second sub-element are disposed in a pattern of concentric circular rings or concentric polygonal rings, and
    wherein the first sub-element is disposed inside the second sub-element.

2. The capacitive micromachined ultrasonic transducer according to claim 1, wherein each of the first detection circuit and the second detection circuit includes a transimpedance circuit.

3. The capacitive micromachined ultrasonic transducer according to claim 1, wherein the cut-off frequency of the first detection circuit is higher than the cut-off frequency of the second detection circuit.

4. The capacitive micromachined ultrasonic transducer according to claim 1, wherein the first electrode of the first cell and the first electrode of the second cell are common, or the second electrode of the first cell and the second electrode of the second cell are common.

5. The capacitive micromachined ultrasonic transducer according to claim 1, wherein a shape of the first cell is the same as a shape of the second cell.

6. The capacitive micromachined ultrasonic transducer according to claim 5, wherein peak frequencies of output currents of the first sub-element and the second sub-element are between a cut-off frequency of the first detection circuit and a cut-off frequency of the second detection circuit, and
    wherein number of the plurality of the first cells of the first sub-element is greater than number of the plurality of the second cells of the second sub-element.

7. The capacitive micromachined ultrasonic transducer according to claim 6, wherein the number of the plurality of the first cells of the first sub element is in the range from 55% to 95% of the number of all the cells is within a range from 55% to 95% of a sum of the number of the plurality of the first cells and the number of the plurality of the second cells.

8. The capacitive micromachined ultrasonic transducer according to claim 5, wherein each of peak frequencies of output currents of the first sub-element and the second sub-element is higher than each of the cut-off frequencies of the first detection circuit and the second detection circuit, and
    wherein number of the plurality of the first cells of the first sub-element is the same as number of the plurality of the second cells of the second sub-element.

9. The capacitive micromachined ultrasonic transducer according to claim 8, wherein the number of the plurality of the first cells is within a range from 25% to 75% of a sum of the number of the plurality of the first cells and the number of the plurality of the second cells.

10. The capacitive micromachined ultrasonic transducer according to claim 1, wherein a ratio of a peak value of reception sensitivity of the first sub-element to a peak value of reception sensitivity of the second sub-element is 0.5 or greater and 0.9 or less.

11. The capacitive micromachined ultrasonic transducer according to claim 1, wherein in at least one of the first sub-element and the second sub-element, a DC voltage is applied to one of the two electrodes, and an AC voltage is applied to the other electrode so that an acoustic wave is transmitted.

12. An information acquisition apparatus comprising:
    the capacitive micromachined ultrasonic transducer according to claim 1;
    a light source configured to emit a light beam; and
    a processing unit,
    wherein the capacitive micromachined ultrasonic transducer detects a photoacoustic wave generated due to the light beam emitted from the light source to a test object and outputs a detection signal, and wherein the processing unit processes the detection signal and acquires information regarding the test object.

13. An information acquisition apparatus comprising:
the capacitive micromachined ultrasonic transducer according to claim 1; and
a processing unit,
wherein the capacitive micromachined ultrasonic transducer is capable of transmitting an ultrasonic wave,
wherein the capacitive micromachined ultrasonic transducer detects an acoustic wave generated by emission of the ultrasonic wave transmitted from the capacitive micromachined ultrasonic transducer to a test object and outputs a detection signal, and
wherein the processing unit processes the detection signal and acquires information regarding the test object.

14. The information acquisition apparatus according to claim 12, wherein the capacitive micromachined ultrasonic transducer is capable of transmitting an ultrasonic wave, and
wherein the information acquisition apparatus further comprises a circuit unit configured to transmit and receive a signal between the capacitive micromachined ultrasonic transducer and the processing unit and a control unit configured to control the processing unit and the circuit unit.

15. The information acquisition apparatus according to claim 12, wherein the processing unit processes the detection signal and acquires image information regarding the test object, and
wherein the information acquisition apparatus further comprises a display unit configured to display an image of the test object.

\* \* \* \* \*